US009433375B2

(12) United States Patent
Saito (10) Patent No.: US 9,433,375 B2
(45) Date of Patent: Sep. 6, 2016

(54) ENDOSCOPE SYSTEM, PROCESSOR DEVICE THEREOF, AND IMAGE PROCESSING METHOD (71) Applicant: FUJIFILM CORPORATION, Tokyo (JP)

(72) Inventor: Takaaki Saito, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 221 days.

(21) Appl. No.: 14/011,957

(22) Filed: Aug. 28, 2013

(65) Prior Publication Data

US 2014/0066733 A1    Mar. 6, 2014

(30) Foreign Application Priority Data

Sep. 4, 2012 (JP) ................. 2012-194180

(51) Int. Cl.
*A61B 5/1455* (2006.01)
*A61B 1/06* (2006.01)
*A61B 5/145* (2006.01)
(Continued)

(52) U.S. Cl.
CPC ....... *A61B 5/14552* (2013.01); *A61B 1/00009* (2013.01); *A61B 1/0638* (2013.01); *A61B 1/0646* (2013.01); *A61B 5/14542* (2013.01); *A61B 5/14551* (2013.01); *G06T 7/408* (2013.01); *G06T 2207/10068* (2013.01); *G06T 2207/10152* (2013.01)

(58) Field of Classification Search
CPC ............ A61B 5/14552; A61B 1/0638; A61B 1/0646; A61B 5/14542; A61B 5/14551; A61B 7/408
See application file for complete search history.

(56) References Cited

U.S. PATENT DOCUMENTS 4,998,973 A    3/1991    Kikuchi
6,413,210 B1   7/2002    Enomoto
(Continued)

FOREIGN PATENT DOCUMENTS

EP    2 465 433 A1    6/2012
JP    63-311937 A     12/1988
(Continued)

OTHER PUBLICATIONS

Extended European Search Report, dated Dec. 18, 2013, for Patent Application No. 13181440.2.
Japanese Notification of Reasons for Refusal for Japanese Application No. 2012-194180, dated Aug. 6, 2014, with a partial English translation.

*Primary Examiner* — Tse Chen
*Assistant Examiner* — Charles G Chiang
(74) *Attorney, Agent, or Firm* — Birch, Stewart, Kolasch & Birch, LLP (57) ABSTRACT In imaging an oxygen saturation level of blood, measurement light having a wavelength of 450 to 500 nm, B light, G light, and an R light are sequentially taken out of broad band light BB emitted from a xenon lamp. An internal body portion is imaged under irradiation with the measurement, B, G, and R light to obtain image data B1, B2, G2, and R2, respectively. A correlation memory stores first and second correlations, each being a correlation among the oxygen saturation level and intensity ratios between the image data B1 and G2 and between the image data R2 and G2. When a cumulative lighting time of the xenon lamp is less than a certain value, the oxygen saturation level is calculated using the first correlation. When the cumulative lighting time equals or exceeds the certain value, the oxygen saturation level is calculated using the second correlation.

8 Claims, 11 Drawing Sheets (51) Int. Cl.
*G06T 7/40* (2006.01)
*A61B 1/00* (2006.01)

(56) References Cited

U.S. PATENT DOCUMENTS

| | | | |
|---|---|---|---|
| 2009/0326384 A1* | 12/2009 | Bigio et al. | A61B 5/0075 600/476 |
| 2012/0053434 A1 | 3/2012 | Saito | |
| 2012/0116192 A1 | 5/2012 | Saito | |
| 2012/0157768 A1 | 6/2012 | Saito | |
| 2012/0157775 A1* | 6/2012 | Yamaguchi | A61B 1/0638 600/180 |

FOREIGN PATENT DOCUMENTS

| | | | | |
|---|---|---|---|---|
| JP | 200465965 A | | 3/2000 | |
| JP | 2000065965 A | * | 3/2000 | ............ G04F 10/00 |
| JP | 2001-112712 A | | 4/2001 | |
| JP | 2010-136775 A | | 6/2010 | |
| JP | 2012-66065 A | | 4/2012 | |
| JP | 2012-193482 A | | 7/2012 | |
| WO | WO 2008/011056 A2 | | 1/2008 | |

* cited by examiner

|  | DISTANCE BETWEEN CONTOUR LINES | | | | |
|---|---|---|---|---|---|
|  | X1 | X2 | X3 | X4 | X5 |
| FIRST CORRELATION | a | b | c | d | e |
| SECOND CORRELATION | f | g | h | i | j |

OXYGEN SATURATION LEVEL (%)

| DISTANCE BETWEEN CONTOUR LINES | | | | |
|---|---|---|---|---|
| X1 | X2 | X3 | X4 | X5 |
| a(T) | b(T) | c(T) | d(T) | e(T) |

FIG. 16

ENDOSCOPE SYSTEM, PROCESSOR DEVICE THEREOF, AND IMAGE PROCESSING METHOD

BACKGROUND OF THE INVENTION

1. Field of the Invention

The present invention relates to an endoscope system that measures an oxygen saturation level of blood, a processor device of the endoscope system, and an image processing method.

2. Description Related to the Prior Art

In a medical field, an endoscope system is widely used for diagnosis and treatment. The endoscope system is constituted of a light source device, an endoscope device, a processor device, a monitor device, and an input device. In use of the endoscope system, an insert section of the endoscope device is introduced into a patient's body cavity. An internal body portion is imaged by an image sensor provided at a distal end portion of the insert section, while being applied with illumination light from the distal end portion. There is known an endoscope system that obtains various types of living body information from an image captured using specific narrow band light as the illumination light.

According to an endoscope system of US Patent Application Publication No. 2012/0116192, for example, an oxygen saturation image, which images an oxygen saturation level of blood on a pixel-by-pixel basis, is produced with the use of narrow band light having a wavelength range in which an absorption coefficient is different between oxyhemoglobin and deoxyhemoglobin as the illumination light. In the oxygen saturation image, a hypoxic region representing a lesion such as cancer and a hyperoxic region representing a normal portion are displayed artificially with different colors. This facilitates grasping the distribution of the cancer at first sight.

To calculate the oxygen saturation level from the captured image, this endoscope system has the correlation among the oxygen saturation level and the intensity ratios of each individual pixel among a plurality of images captured under irradiation with a plurality of types of narrow band light, as data stored in advance in a memory such as a LUT. The oxygen saturation level is calculated using this correlation.

In this system, the correlation among the oxygen saturation level and the intensity ratios is obtained on the precondition that the difference in absorptance (absorption coefficient) between oxyhemoglobin and deoxyhemoglobin under irradiation with the narrow band light is invariable. For this reason, in the case of using a light source whose emission spectrum varies with time e.g. a xenon lamp, the difference in absorptance between oxyhemoglobin and deoxyhemoglobin deviates from a specified value with a lapse of time. Also, in the case of using a light source having a phosphor (for example, a phosphor absorbing blue excitation light and emitting green to red fluorescence) whose emission spectrum varies with temperature variation, the difference in absorptance between oxyhemoglobin and deoxyhemoglobin deviates from the specified value due to the temperature variation. Such deviation causes miscalculation of the oxygen saturation level.

SUMMARY OF THE INVENTION

An object of the present invention is to provide an endoscope system that can precisely measure an oxygen saturation level even if an emission spectrum of illumination light is variable, a processor device of the endoscope system, and an image processing method.

To achieve the above and other objects of the present invention, an endoscope system includes a lighting section, an image information obtaining section, an oxygen saturation level calculating section, a spectrum information obtaining section, and a changing section. The lighting section applies first illumination light to an object. The first illumination light has a first wavelength band in which oxyhemoglobin and deoxyhemoglobin have different absorption coefficients. The image information obtaining section images the object, and obtains first image information under irradiation with the first illumination light. The oxygen saturation level calculating section calculates an oxygen saturation level of blood based on the first image information. The spectrum information obtaining section obtains spectrum information of the first illumination light. The changing section changes a calculation method of the oxygen saturation level based on the spectrum information of the first illumination light.

It is preferable that the lighting section further applies second illumination light having a second wavelength band and third illumination light having a third wavelength band to the object. It is preferable that the image information obtaining section further obtains second image information under irradiation with the second illumination light and third image information under irradiation with the third illumination light. The oxygen saturation level calculating section includes a correlation memory and an oxygen saturation level calculator. The correlation memory stores a correlation among the oxygen saturation level, a first intensity ratio being an intensity ratio of each pixel between a first image information pair chosen out of the first to third image information, and a second intensity ratio being an intensity ratio of each pixel between a second image information pair different from the first image information pair. The oxygen saturation level calculator calculates the oxygen saturation level by using the first to third image information and the correlation.

The first wavelength band is preferably 400 to 500 nm. The second wavelength band is preferably 590 to 700 nm, and the third wavelength band is preferably 540 to 580 nm.

The correlation memory may store a plurality of correlations. The changing section may choose one of the correlations based on the spectrum information obtained by the spectrum information obtaining section. Alternatively, the changing section may update the correlation based on the spectrum information obtained by the spectrum information obtaining section.

The spectrum information is preferably spectrum change information relating to change in a spectrum of the first illumination light. A cumulative lighting time of the lighting section may be used as the spectrum change information. A deviation between a measurement value and a predetermined initial value of at least one of the first and second intensity ratios may be used as the spectrum change information.

The lighting section preferably has a xenon lamp.

A processor device of an endoscope system according to the present invention includes a reception section for receiving the image information, an oxygen saturation level calculating section for calculating an oxygen saturation level of blood based on the image information, a spectrum information obtaining section for obtaining spectrum information of the illumination light, and a changing section for changing a calculation method of the oxygen saturation level based on the spectrum information of the illumination light.

An image processing method according to the present invention includes the steps of calculating an oxygen saturation level of blood based on the image information, obtaining spectrum information of the illumination light, and changing a calculation method of the oxygen saturation level based on the obtained spectrum information of the illumination light.

According to the present invention, the calculation method of the oxygen saturation level is changed based on the spectrum information of the illumination light. Therefore, even if an emission spectrum of the illumination light varies with a lapse of time or temperature variation, it is possible to measure the oxygen saturation level with high accuracy.

BRIEF DESCRIPTION OF THE DRAWINGS

For more complete understanding of the present invention, and the advantage thereof, reference is now made to the subsequent descriptions taken in conjunction with the accompanying drawings, in which.

DESCRIPTION OF THE PREFERRED EMBODIMENTS

First Embodiment

Figure 1:
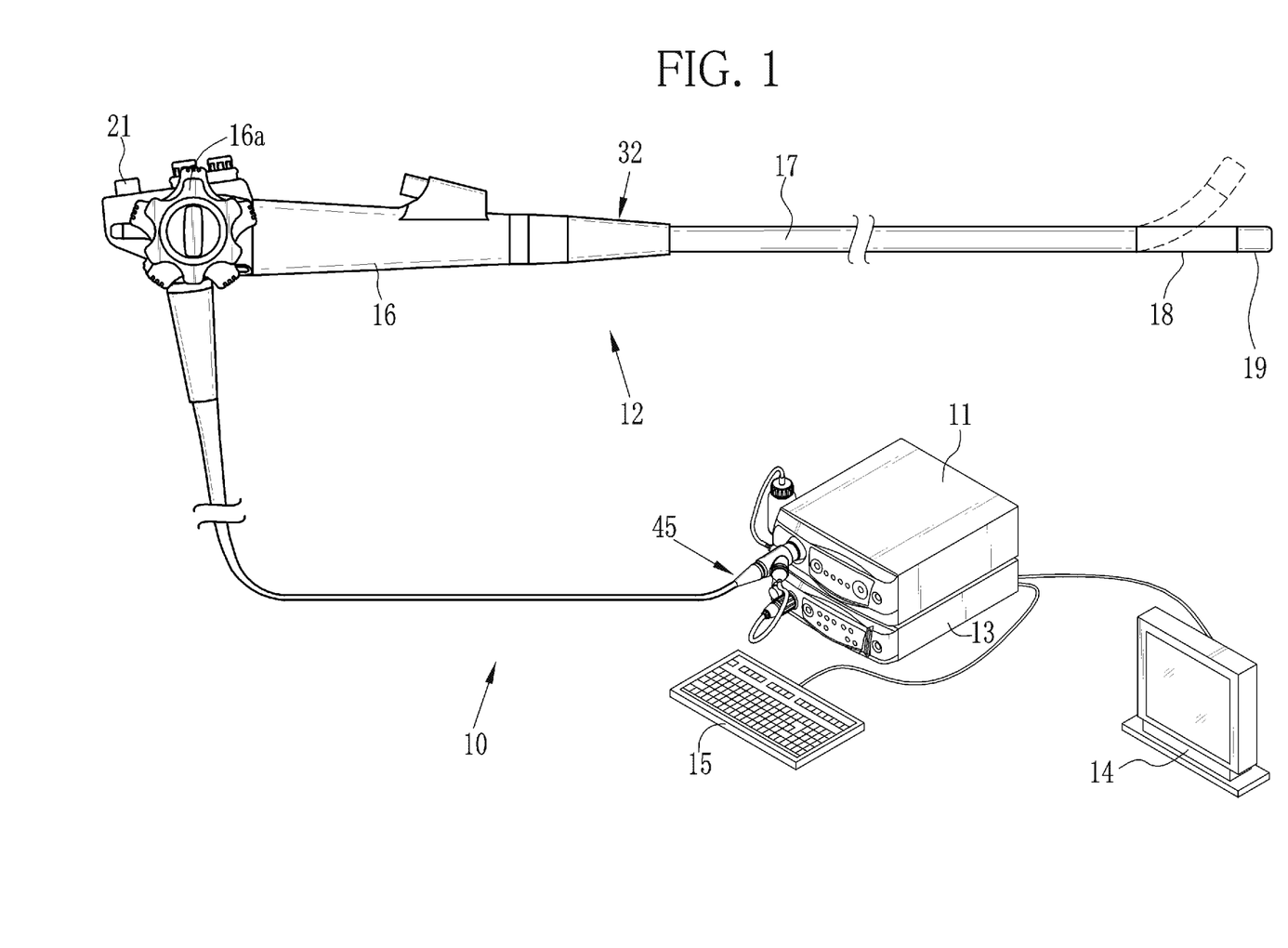
FIG. 1 is a schematic perspective view of an endoscope system.

As shown in FIG. 1, an endoscope system 10 is constituted of a light source device 11, an endoscope device 12, a processor device 13, a color monitor device 14, and an input device 15 including a keyboard and the like. The light source device 11 emits illumination light to irradiate an interior of a patient's body. The endoscope device 12 images an internal body portion, while applying the illumination light emitted from the light source device 11 to the internal body portion. The processor device 13 applies image processing to image data obtained by the endoscope device 12. An endoscopic image after being subjected to the image processing is displayed on the color monitor device 14.

The endoscope device 12 includes a flexible elongated portion 17, a steering assembly 18, and a head assembly 19 disposed in this order from the side of a control handle unit 16. The flexible elongated portion 17 is slender and bendable. The steering assembly 18 is curved by a turn of an angle knob 16a provided on the control handle unit 16. Turning the steering assembly 18 to an arbitrary direction and an arbitrary angle makes the head assembly 19 aim at a desired body portion to be examined.

The endoscope system 10 is switchable between a normal mode and an oxygen saturation level measurement mode for observing an oxygen saturation level of blood. In the normal mode, a normal image that is captured under irradiation with visible light (white light) having a wavelength band ranging from blue to red is displayed on the monitor device 14. In the oxygen saturation level measurement mode, an oxygen saturation image (special image), which images the oxygen saturation level of blood, is displayed on the monitor device 14. Mode switching is performed by the input device 15 or a mode switch 21 provided in the endoscope device 12.

Figure 2:
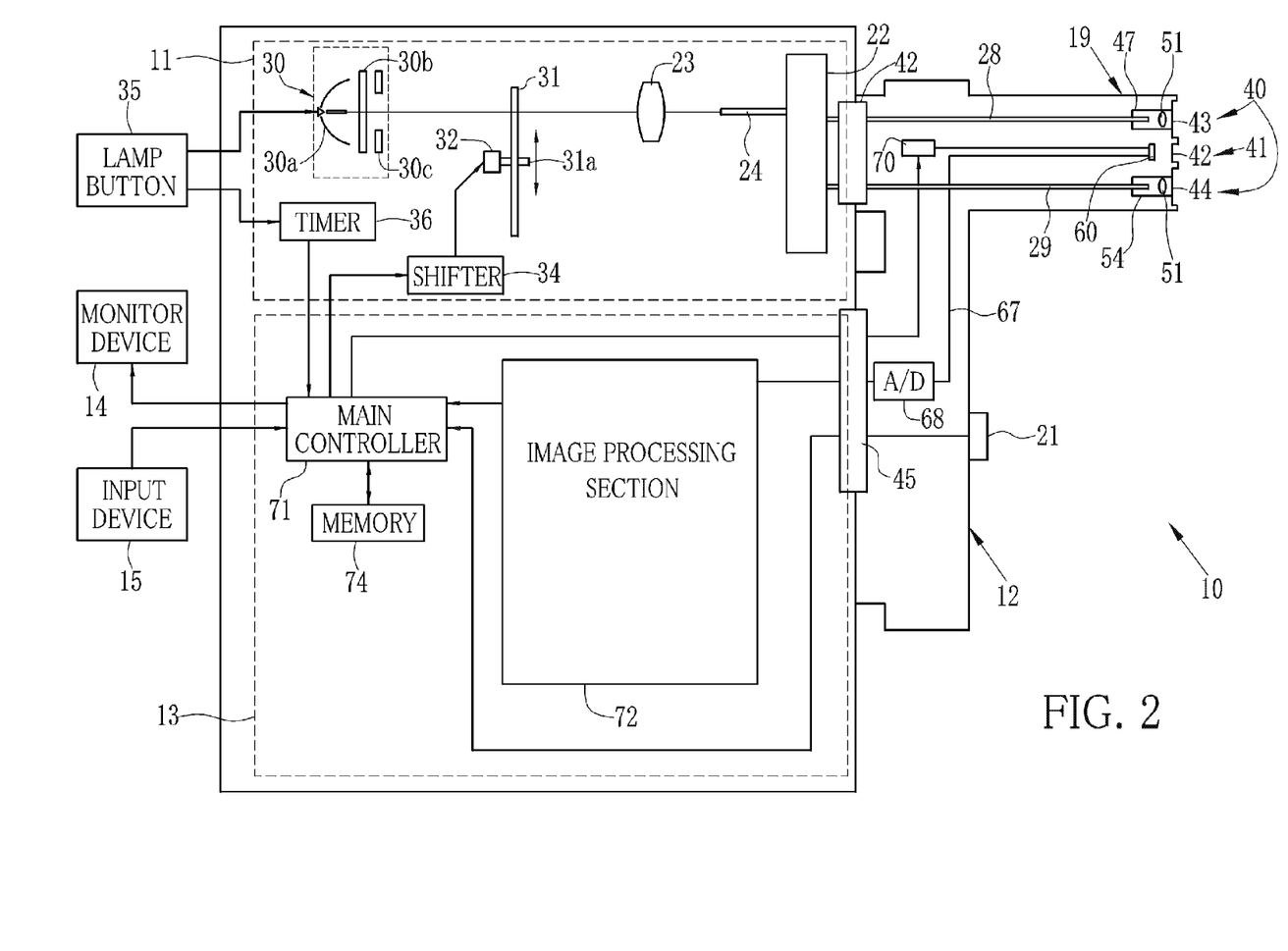
FIG. 2 is a block diagram of an example of the endoscope system.

As shown in FIG. 2, the light source device 11 includes a white light source unit 30, a rotary filter 31, a motor 32, and a shifter 34. The rotary filter 31 performs wavelength separation of broad band light BB emitted from the white light source unit 30. The motor 32 is coupled to a rotary shaft 31a of the rotary filter 31 to rotate the rotary filter 31 at a constant rotation speed. The shifter 34 shifts the rotary filter 31 in its radial direction.

Figure 3:
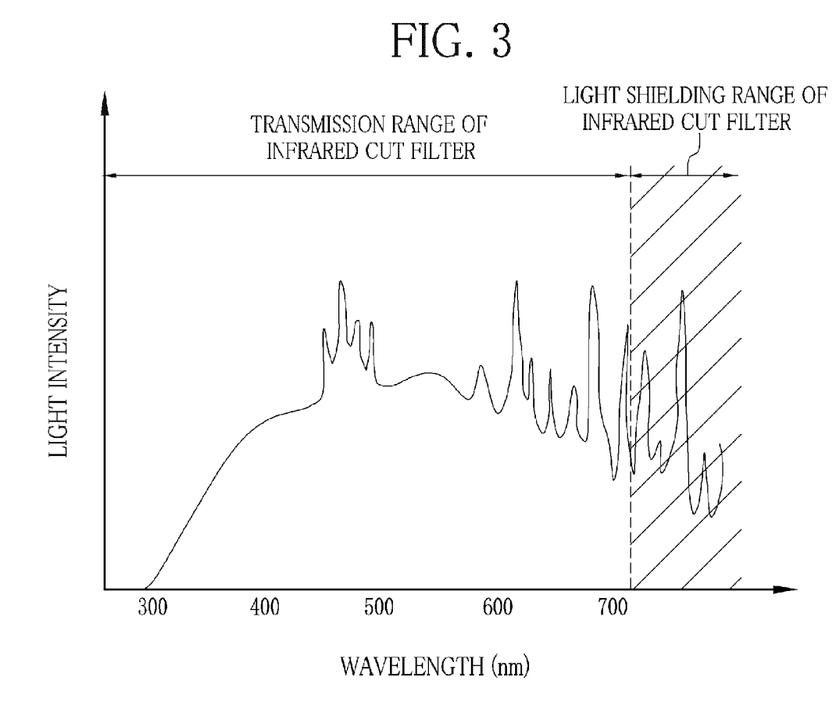
FIG. 3 is a graph showing an emission spectrum of a xenon lamp.

The white light source unit 30 includes a white light source 30a, an infrared cut filter 30b, and an aperture stop 30c. The white light source 30a, being composed of a xenon lamp, emits the broad band light BB having an emission spectrum shown in FIG. 3. The emission spectrum of the broad band light BB varies with change in a light-emitting property of the white light source 30a with a lapse of time. In other words, the longer a cumulative lighting time of the xenon lamp, the larger variation in the emission spectrum of the broad band light BB becomes. There is the correlation between the cumulative lighting time of the xenon lamp and the variation in the emission spectrum of the broad band light BB. Therefore, in a first embodiment, the cumulative lighting time of the xenon lamp is used as emission spectrum variation data of the broad band light BB.

The white light source 30a turns on and off by operation of a lamp button 35. This lamp button 35 is connected to a timer 36 provided in the light source device 11. Whenever the lamp button 35 is operated, the timer 36 measures how long the lamp button 35 is turned on to obtain the cumulative lighting time T of the white light source 30a. Data of the cumulative lighting time T is sent to the processor device 13.

The infrared cut filter 30b is disposed between the white light source 30a and the aperture stop 30c. The infrared cut filter 30b transmits light having a wavelength band of 720 nm or less, while blocks light having a wavelength band of more than 720 nm (see FIG. 3). The aperture stop 30c regulates the amount of the broad band light BB that has exit from the white light source unit 30 and is entering the rotary filter 31 by controlling the degree of opening. Note that, the white light source 30a is not limited to the xenon lamp, as long as its emission spectrum varies with a lapse of time. The white light source 30a may include a phosphor emitting fluorescence the emission spectrum of which varies with a lapse of time. For example, in the case of using a light source having a phosphor that emits green to red fluorescence by application of blue excitation light, broad band light BB including the blue excitation light and the fluorescence is emitted.

Figure 4:
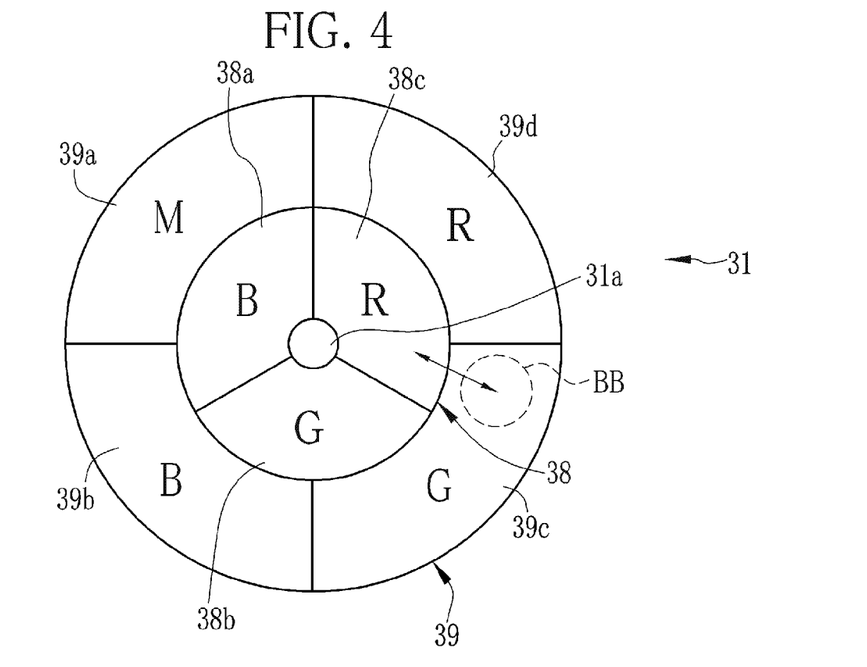
FIG. 4 is a plan view of a rotary filter.

As shown in FIG. 4, the rotary filter 31 rotates about the rotary shaft 31a coupled to the motor 32. The rotary filter 31 is provided with a first filter portion 38 and a second filter portion 39 disposed in this order along its radial direction from the center of the rotary filter 31 where the rotary shaft 31a is situated. The shifter 34 shifts the rotary filter 31 in its radial direction such that an optical path of the broad band light BB passes through the first filter portion 38 in the normal mode. The optical path of the broad band light BB passes through the second filter portion 39 in the oxygen saturation level measurement mode.

Figure 5:
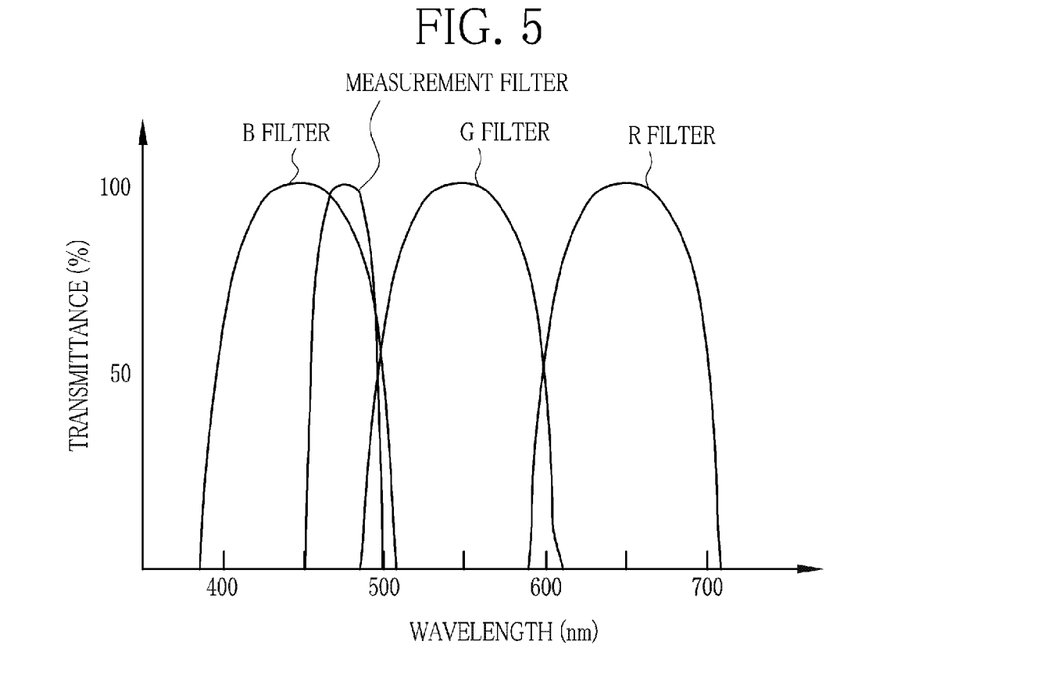
FIG. 5 is a graph showing spectral transmittance of a measurement filter, a B filter, a G filter, and an R filter.

The first filter portion 38 has a B filter 38a, a G filter 38b, and an R filter 38c. Each of the B, G, and R filters 38a to 38c has the shape of a sector having a central angle of 120°. As shown in FIG. 5, the B filter 38a transmits B light in a blue wavelength band (380 to 520 nm) out of the broad band light BB. The G filter 38b transmits G light in a green wavelength band (480 to 620 nm). The R filter 38c transmits R light in a red wavelength band (580 to 720 nm). Thus, in the normal mode, the B, G, and R light is sequentially emitted by the rotation of the rotary filter 31. The B, G, and R light enters light guides 28 and 29 of the endoscope device 12 through a condenser lens 23 and an optical fiber 24.

The second filter portion 39 is provided with a measurement filter 39a (symbolized by "M" in FIG. 4), a B filter 39b, a G filter 39c, and an R filter 39d. The measurement filter 39a transmits measurement light for use in measurement of the oxygen saturation level out of the broad band light BB. The measurement light is in a wavelength band of 450 to 500 nm at which the difference in absorptance between oxyhemoglobin and deoxyhemoglobin is relatively large (see FIG. 10). The B, G, and R filters 39b to 39d have the same transmission properties as the B, G, and R filters 38a to 38c, and transmit the B, G, and R light, as described above. Therefore, in the oxygen saturation level measurement mode, the measurement, B, G, and R light is sequentially emitted by the rotation of the rotary filter 31. These four types of light sequentially enter the light guides 28 and 29 through the condenser lens 23 and the optical fiber 24.

As shown in FIG. 2, the endoscope device 12 being an electronic endoscope is provided with a lighting section 40 and an imaging section 41. The lighting section 40 applies two beams of light led through the light guides 28 and 29 to the internal body portion. The imaging section 41 captures an image of the internal body portion.

The lighting section 40 has two lighting windows 43 and 44 disposed on both sides of the imaging section 41. Light projection units 47 and 54 are contained in the recess of the lighting windows 43 and 44, respectively. The light projection units 47 and 54 apply the light led through the light guides 28 and 29 to the internal body portion through lighting lenses 51, respectively. The imaging section 41 has an imaging window 42 positioned at approximately the center of the head assembly 19. The light reflected from the internal body portion passes through the imaging window 42.

In the recess of the imaging window 42, there is provided an optical system such as an objective lens unit (not shown) for capturing image light of the internal body portion. An image sensor 60 e.g. a CCD (charge coupled device) is provided behind the objective lens unit to produce an image signal from the image light. This image sensor 60 is a monochrome image sensor, which has no color filter on its pixels. The image sensor 60 receives the light from the objective lens unit at its light receiving surface (imaging surface), and performs photoelectric conversion of the received light to output an analog image signal. An IT (interline transfer) type CCD is used as the image sensor 60, but a CMOS (complementary metal-oxide semiconductor) having a global shutter may be used instead.

The analog image signal outputted from the image sensor 60 is inputted to an A/D converter 68 through a scope cable 67. The A/D converter 68 converts the analog image signal into digital image data in accordance with its voltage level. The converted image data is inputted to the processor device 13 through a connector 45.

Figure 6A:
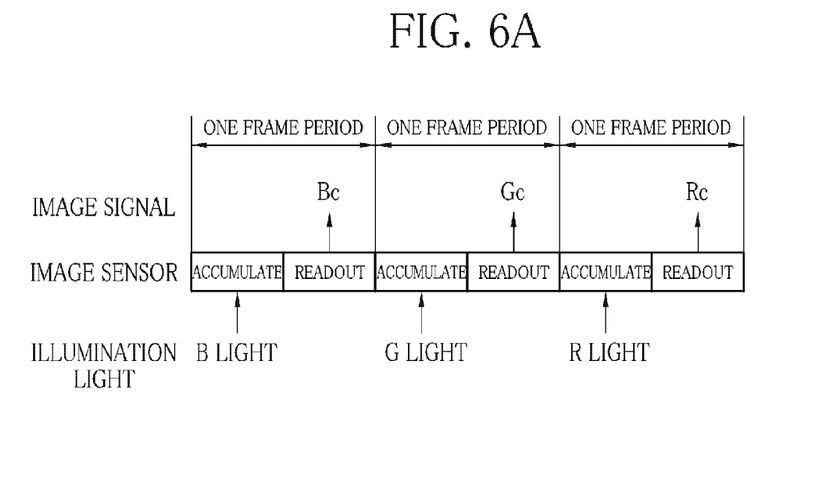
FIG. 6A is an explanatory view of the operation of an image sensor in a normal mode.
Figure 6B:
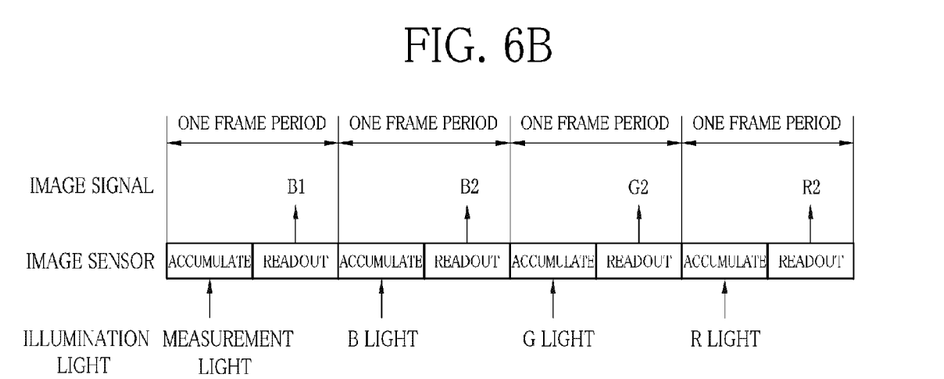
FIG. 6B is an explanatory view of the operation of the image sensor in an oxygen saturation level measurement mode.

An imaging controller 70 controls the image sensor 60 in accordance with the mode of the endoscope system 10. In the normal mode, as shown in FIG. 6A, the image sensor 60 captures image light under irradiation with the B, G, and R light, and accumulates electric charge. Based on the accumulated electric charge, a blue signal Bc, a green signal Gc, and a red signal Rc are sequentially outputted. This sequential operation is repeated as long as the endoscope system 10 is in the normal mode. The blue, green, and red signals Bc, Gc, and Rc are converted into blue, green, and red image data Bc, Gc, and Rc by the A/D conversion. In the oxygen saturation level measurement mode, on the other hand, as shown in FIG. 6B, the image sensor 60 captures image light under irradiation with the measurement, B, G, and R light, and accumulates electric charge. Based on the accumulated electric charge, a measurement blue signal B1, a blue signal B2, a green signal G2, and a red signal R2 are sequentially outputted. This sequential operation is repeated as long as the endoscope system 10 is in the oxygen saturation level measurement mode. The measurement blue, blue, green, and red signals B1, B2, G2, and R2 are converted into measurement blue, blue, green, and red image data B1, B2, G2, and R2, respectively, by the A/D conversion.

The processor device 13 is provided with a reception section (not shown) for receiving the image data from the endoscope device 12, a main controller 71, an image processing section 72, and a memory 74. The monitor device 14 and the input device 15 are connected to the main controller 71. The main controller 71 controls each part of the processor device 13, and additionally controls the operation of the imaging controller 70 of the endoscope device 12 and the monitor device 14 based on information inputted from the mode switch 21 of the endoscope device 12 and the input device 15.

Figure 7:
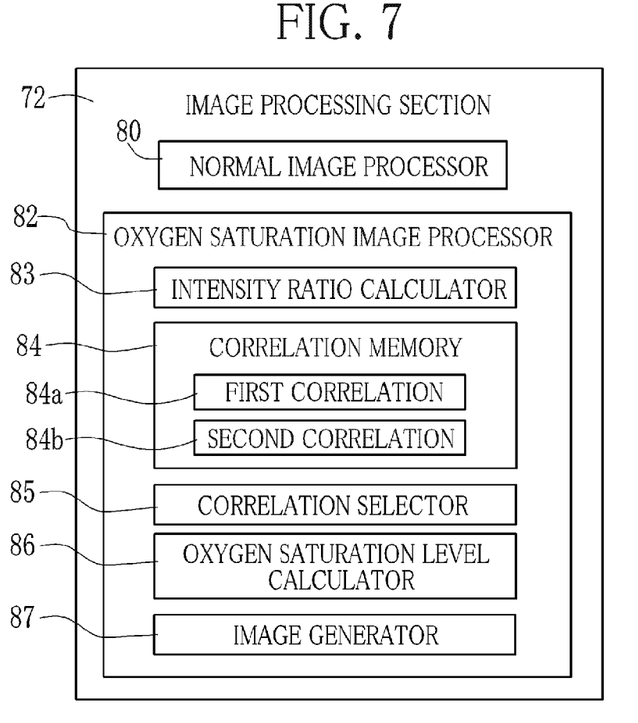
FIG. 7 is a block diagram of an image processing section according to a first embodiment.

As shown in FIG. 7, the image processing section 72 includes a normal image processor 80 and an oxygen saturation image processor 82. The normal image processor 80 assigns the blue, green, and red image data Bc, Gc, and Rc to B, G, and R channels of the monitor device 14, respectively. Thus, a normal image is displayed on the monitor device 14.

The oxygen saturation image processor 82 includes an intensity ratio calculator 83, a correlation memory 84, a correlation selector 85, an oxygen saturation level calculator 86, and an image generator 87. The intensity ratio calculator 83 calculates the intensity ratio B1/G2 between the measurement blue image data B1 and the green image data G2 and the intensity ratio R2/G2 between the green image data G2 and the red image data R2 with the use of the image data obtained in the oxygen saturation level measurement mode. The intensity ratio calculator 83 calculates the intensity ratios of each individual pixel located in the same position among the image data. The intensity ratios of each and every pixel included in the image data or only the pixels of a blood vessel area may be calculated. In this case, the blood vessel area is determined based on difference in the image data between the blood vessel area and the other area.

Figure 8:
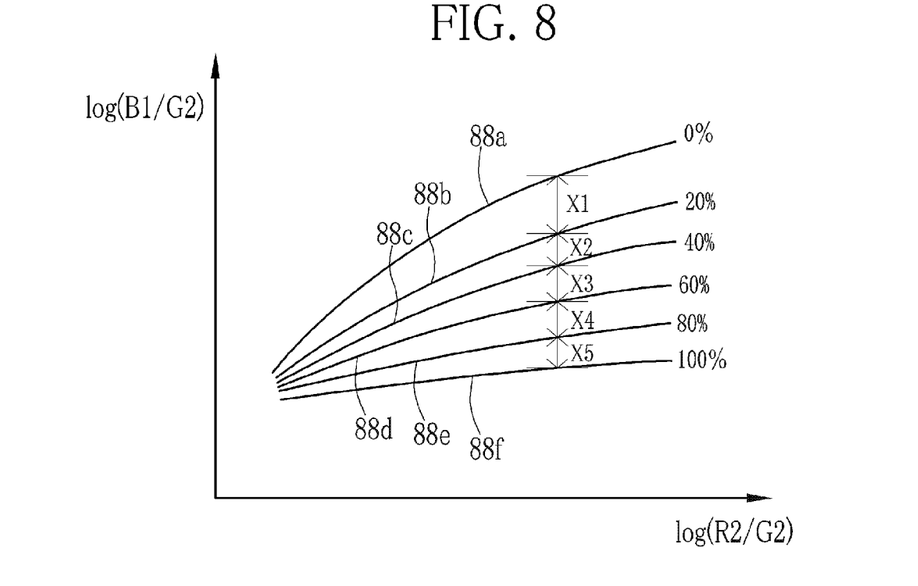
FIG. 8 is a graph showing the correlation among an oxygen saturation level and intensity ratios B1/G2 and R2/G2.

The correlation memory 84 stores the correlation among the oxygen saturation level and the intensity ratios B1/G2 and R2/G2. As shown in FIG. 8, the correlation is in the form of a two dimensional table in which contour lines representing the oxygen saturation level are defined in two-dimensional space. The position and shape of the contour lines are determined by physical simulation of light scattering, and variable in accordance with blood volume. The intensity ratios B1/G2 and R2/G2 are in a log scale.

It is defined that each of the distances X1 to X5 between the two adjacent contour lines depends on the difference in the absorption coefficient between oxyhemoglobin and deoxyhemoglobin at the wavelength band of the measurement light. In this embodiment, since the xenon lamp the emission spectrum of which varies with a lapse of time is used as the light source, the difference in the absorption coefficient between oxyhemoglobin and deoxyhemoglobin changes according to the variation in the emission spectrum of the xenon lamp with a lapse of time. In order to deal with the variation with time, the correlation memory 84 stores first and second correlations 84a and 84b. The first correlation 84a is used when the cumulative lighting time is less than a certain value and the difference in the absorption coefficient between oxyhemoglobin and deoxyhemoglobin is within a certain predetermined range. The second correlation 84b is used when the cumulative lighting time equals or exceeds the certain value and the difference in the absorption coefficient between oxyhemoglobin and deoxyhemoglobin is out of the certain predetermined range.

Figure 9:
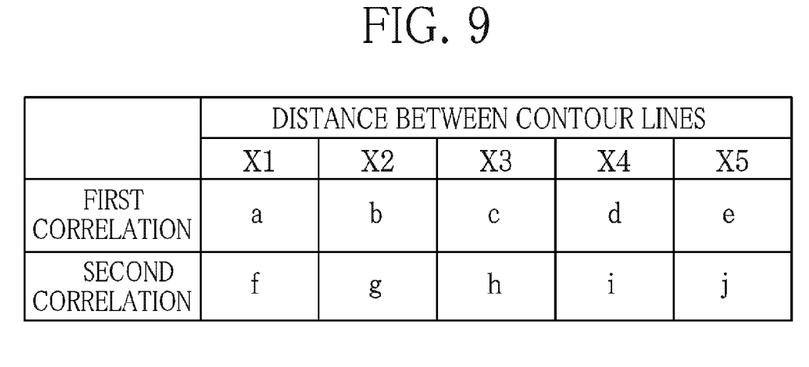
FIG. 9 is a table listing the distances X1 to X5 of contour lines in each of first and second correlations.

As shown in FIG. 9, according to the first correlation 84a, the distance X1 between a contour line 88a representing an oxygen saturation level of 0% and a contour line 88b representing an oxygen saturation level of 20% is determined at "a". The distance X2 between the contour line 88b representing an oxygen saturation level of 20% and a contour line 88c representing an oxygen saturation level of 40% is determined at "b". The distance X3 between the contour line 88c representing an oxygen saturation level of 40% and a contour line 88d representing an oxygen saturation level of 60% is determined at "c". The distance X4 between the contour line 88d representing an oxygen saturation level of 60% and a contour line 88e representing an oxygen saturation level of 80% is determined at "d". The distance X5 between the contour line 88e representing an oxygen saturation level of 80% and a contour line 88f representing an oxygen saturation level of 100% is determined at "e". Likewise, according to the second correlation 84b, the distance X1 is determined at "f" that differs from "a". The distance X2 is determined at "g" that differs from "b". The distance X3 is determined at "h" that differs from "c". The distance X4 is determined at "i" that differs from "d". The distance X5 is determined at "j" that differs from "e". Note that, "a" to "j" are constants.

Figure 10:
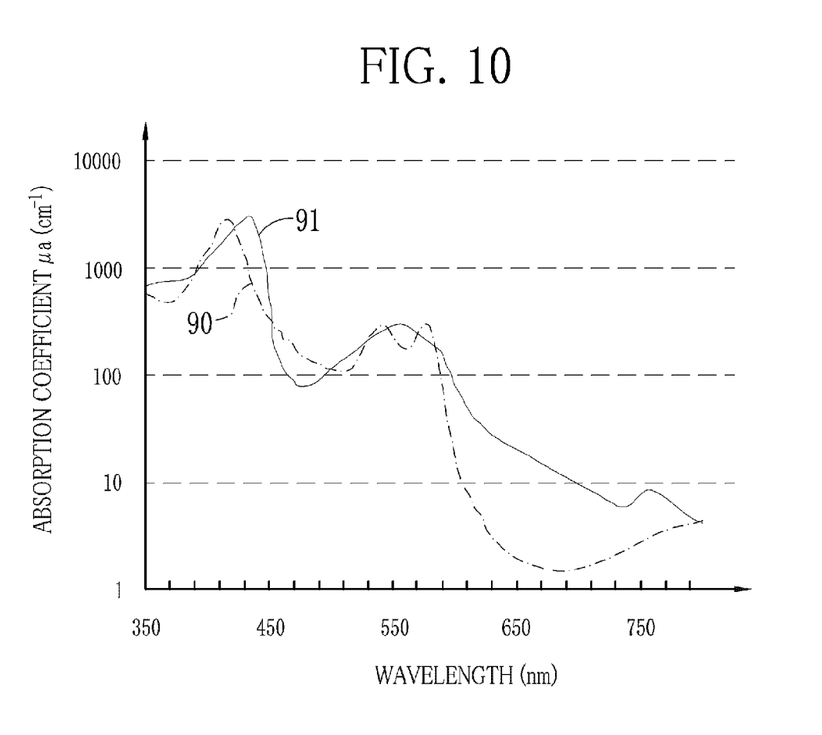
FIG. 10 is a graph showing an absorption coefficient of oxyhemoglobin and deoxyhemoglobin in a wavelength band ranging from 350 to 800 nm.

The first and second correlations 84a and 84b closely relates to the absorption property of oxyhemoglobin and deoxyhemoglobin and a light scattering property. Referring to FIG. 10, a curve 90 represents the absorption coefficient of oxyhemoglobin, and a curve 91 represents the absorption coefficient of deoxyhemoglobin. For example, the use of a wavelength of 473 nm at which the absorption coefficient largely differs between oxyhemoglobin and deoxyhemoglobin allows the obtainment of information about the oxygen saturation level. However, the measurement blue image data B1 including a wavelength component of 473 nm is highly dependent not only on the oxygen saturation level but also on the blood volume. For this reason, the use of the intensity ratios B1/G2 and R2/G2, which are calculated from the measurement blue image data B1, the red image data R2 mainly depending on the blood volume, and the green image data G2 being a reference image (standardization image data) of the blue and red image data B2 and R2, allows the obtainment of the oxygen saturation level with high accuracy with eliminating the influence of the blood volume.

Light having a wavelength band of 470 to 700 nm has a small scattering coefficient and small wavelength dependence in mucosal tissue. Thus, using the light of this wavelength band as the illumination light allows obtaining blood information, including the blood volume and the oxygen saturation level, with reducing the influence of the depth of a blood vessel. For this reason, the measurement blue image data preferably has a component having a wavelength band of 450 to 500 nm. The green image data preferably has a component having a wavelength band of 540 to 580 nm. The red image data preferably has a component having a wavelength band of 590 to 700 nm.

Note that, the correlation memory 84 may also store the correlation between the blood volume and the intensity ratio R2/G2. This correlation is in the form of a one dimensional table in which the blood volume increases with increase in the intensity ratio R2/G2. The correlation between the blood volume and the intensity ratio R2/G2 is used in calculating the blood volume.

The correlation selector 85 selects one of the first and second correlations 84a and 84b stored in the correlation memory 84 as a correlation to be used in the oxygen saturation level calculator 86. The correlation selector 85 selects the first correlation 84a, when the cumulative lighting time T measured by the timer 36 of the light source device 11 is less than the certain value. The correlation selector 85 selects the second correlation 84b, when the cumulating lighting time T equals or exceeds the certain value.

The oxygen saturation level calculator 86 calculates the oxygen saturation level of each pixel with the use of one of the first and second correlations 84a and 84b selected by the correlation selector 85 and the intensity ratios B1/G2 and R2/G2 calculated by the intensity ratio calculator 83. In the following description, B1*, G2*, and R2* represent the intensity of a certain pixel in the measurement blue image data B1, the green image data G2, and the red image data R2, respectively, to be used in the calculation of the oxygen saturation level. More specifically, the intensity ratios of each pixel are represented by B1*/G2* and R2*/G2*.

Figure 11:
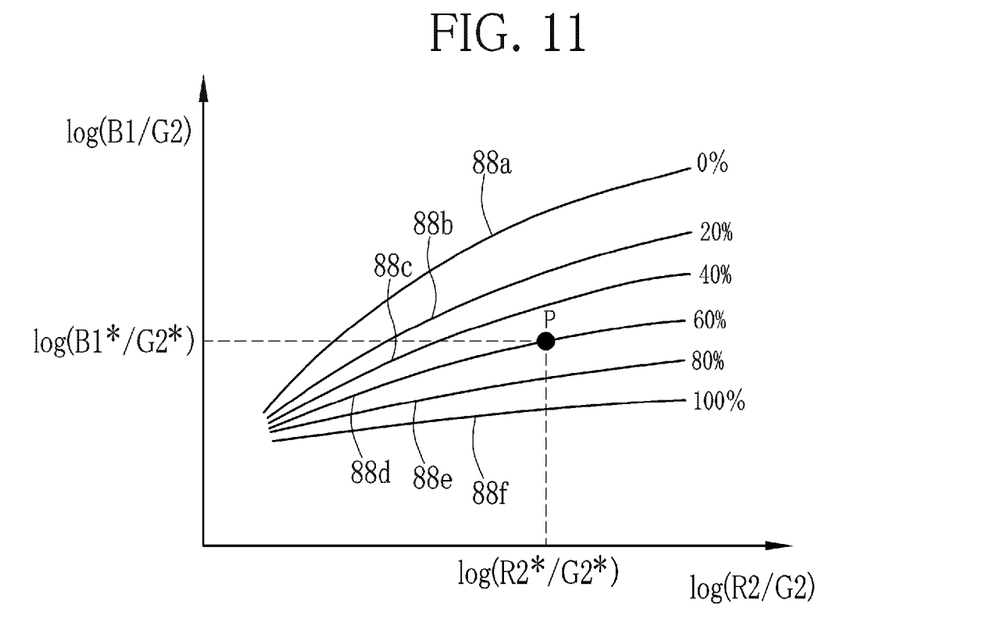
FIG. 11 is a graph for explaining a calculation method of the oxygen saturation level from intensity ratios B1*/G2* and R2*/G2*.

As shown in FIG. 11, the oxygen saturation level calculator 86 determines a point P corresponding to the intensity ratios B1*/G2* and R2*/G2* in the correlation stored in the correlation memory 85. When the point P is situated between the contour line 88a representing an oxygen saturation level of 0% and the contour line 88f representing an oxygen saturation level of 100%, the point P indicates the percentile of the oxygen saturation level. Taking FIG. 11 as an example, the point P is positioned in the contour line 88d, so the oxygen saturation level is known to be 60%.

If the point is out of the range between the contour lines 88a and 88f, and more specifically if the point is positioned above the contour line 88a, the oxygen saturation level is determined to be 0%. If the point is positioned below the contour line 88f, the oxygen saturation level is determined to be 100%. Note that, in a case where the point is out of the range between the contour lines 88a and 88f, the oxygen saturation level of that pixel may be judged to be unreliable and not to be displayed on the monitor device 14.

The image generator 87 produces the oxygen saturation image, which images the oxygen saturation level, with the use of the oxygen saturation level calculated by the oxygen saturation level calculator 86 and the blue image data B2, the green image data G2, and the red image data R2 obtained in the oxygen saturation level measurement mode. The image generator 87 multiplies the blue, green, and red image data B2, G2, and R2 by a gain corresponding to the oxygen saturation level.

Figure 12:
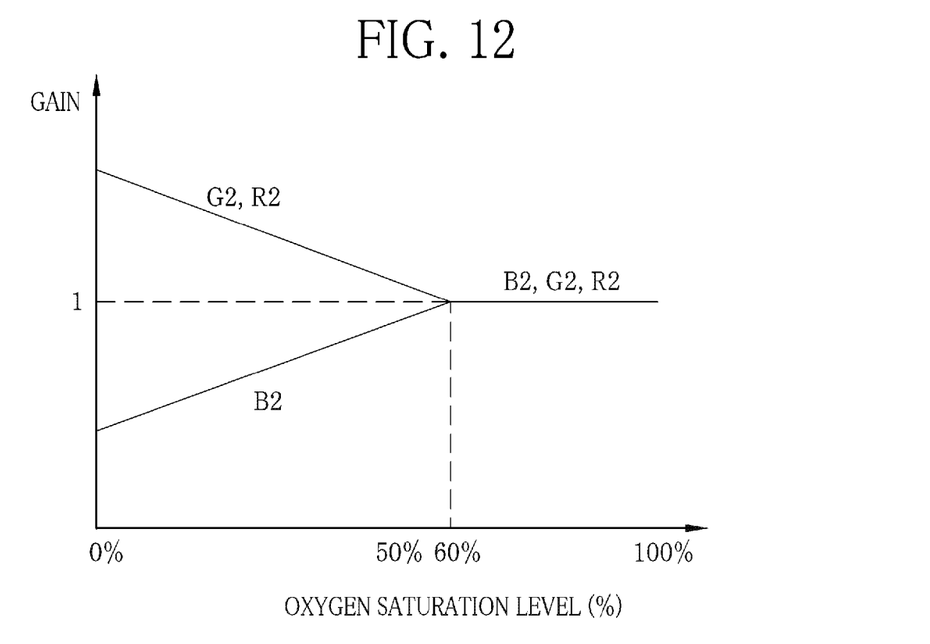
FIG. 12 is a graph showing the relation between a gain and image data B2, G2, and R2.

As shown in FIG. 12, when the oxygen saturation level is 60% or more, the blue, green, and red image data B2, G2, and R2 is multiplied by a gain "1". On the contrary, when the oxygen saturation level is less than 60%, the blue image data B2 is multiplied by a gain less than "1" and the green and red image data G2 and R2 is multiplied by a gain more than "1". The blue, green, and red image data B2, G2, and R2 after being subjected to the gain processing is assigned to the B, G, and R channels of the monitor device 14, respectively.

The oxygen saturation image produced as described above is displayed on the monitor device 14. By the gain processing, a hypoxic region in which the oxygen saturation level is less than a certain value (60% in this embodiment) is displayed with an appropriate artificial color, while a hyperoxic region is displayed with a normal original color, just as with the normal image. Note that, the hyperoxic region having an oxygen saturation level of 60 to 100% may be also displayed with artificial colors different from those of the hypoxic region.

As described above, the intensity ratio calculator 83, the correlation memory 84, and the oxygen saturation level calculator 86 of the image processing section 72 compose an oxygen saturation level calculating section. The timer 36 for measuring the cumulative lighting time of the xenon lamp corresponds to a spectrum information obtaining section. The correlation selector 85, which selects one of the first and second correlations in accordance with the cumulative lighting time, is an example of a changing section for changing a calculation method of the oxygen saturation level.

Figure 13:
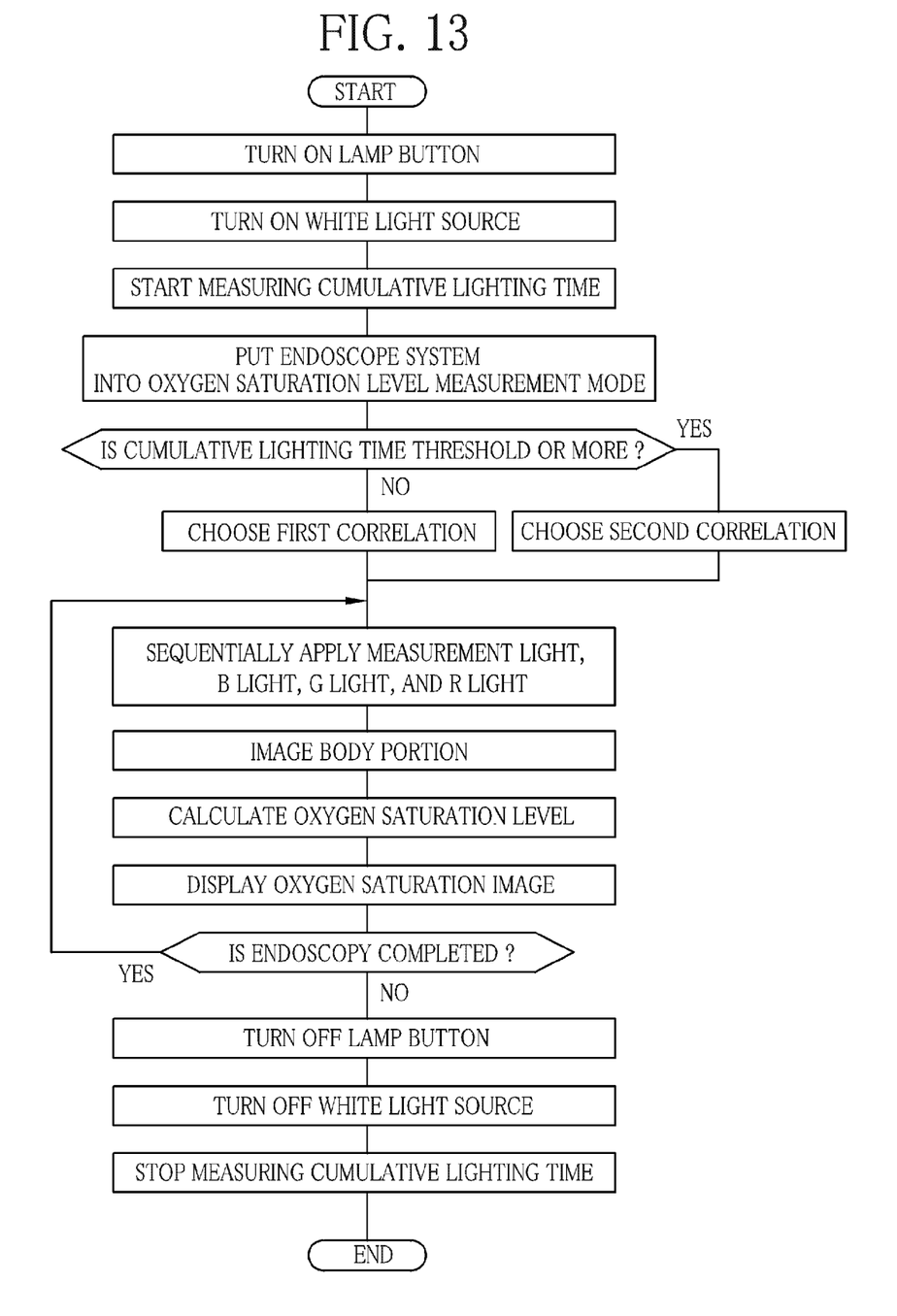
FIG. 13 is a flowchart of the endoscope system in the oxygen saturation level measurement mode.

Next, an operation flow of the endoscope system 10 in the oxygen saturation level measurement mode will be described with referring to a flowchart of FIG. 13. When the lamp button 35 is switched on, the white light source 30a being the xenon lamp is turned on, and the timer 36 starts measuring the cumulative lighting time T. The endoscope system 10 is put into the oxygen saturation level measurement mode by operation of the mode switch 21 of the endoscope device 12. Thus, the measurement, B, G, and R light is sequentially applied to the internal body portion, and the monochrome image sensor 60 captures images in synchronization with the application of the light. When the cumulative lighting time T measured by the timer 36 is less than the certain value, the first correlation 84a is chosen for use in the calculation of the oxygen saturation level. When the cumulative lighting time T equals or exceeds the certain value, on the other hand, the second correlation 84b is chosen.

After that, the intensity ratio B1/G2 between the measurement blue image data B1 and the green image data G2 and the intensity ratio R2/G2 between the red image data R2 and the green image data G2 are calculated on a pixel-by-pixel basis. The oxygen saturation level of each pixel is obtained from the two intensity ratios B1/G2 and R2/G2 and the first or second correlation chosen in accordance with the cumulative lighting time T. Based on the obtained oxygen saturation level and the blue, green, and red image data B2, G2, and R2, the oxygen saturation image is produced and displayed on the monitor device 14. This sequential flow from the application of the illumination light and the display of the oxygen saturation image is repeated during the oxygen saturation level measurement mode. When endoscopy is completed, the lamp button 35 is switched off. Thus, the white light source 30a is turned off, and the timer 36 stops measuring the cumulative lighting time T.

Second Embodiment

In the above first embodiment, one of the two correlations is used for calculating the oxygen saturation level in accordance with the cumulative lighting time of the xenon lamp. In a second embodiment, the distances X1 to X5 are changed based on the cumulative lighting time of the xenon lamp to update the correlation.

Figure 14:
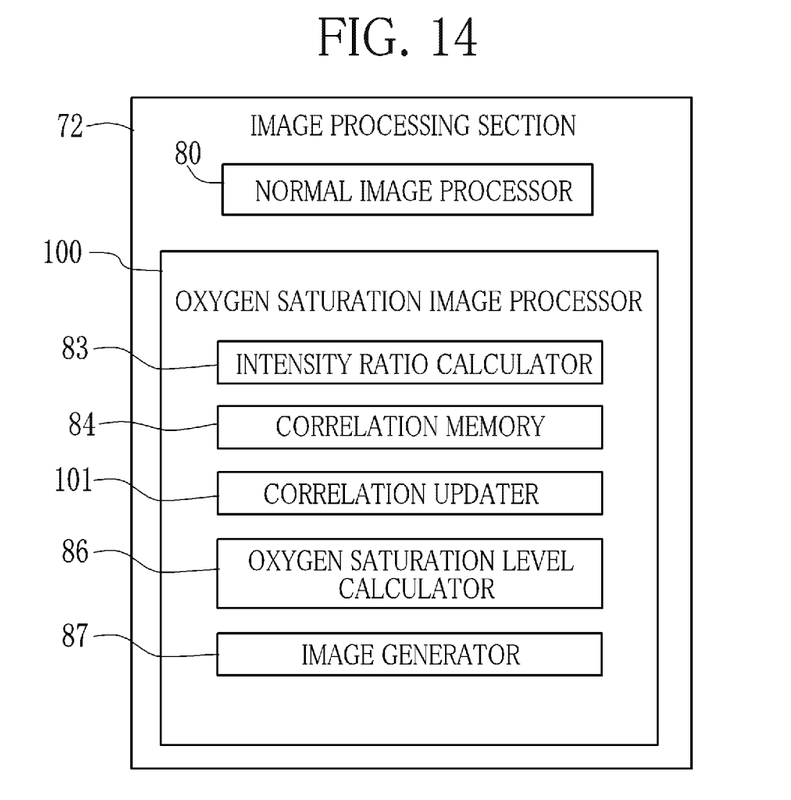
FIG. 14 is a block diagram of an image processing section according to a second embodiment.

In the second embodiment, as shown in FIG. 14, an oxygen saturation image processor 100 is used instead of the oxygen saturation image processor 82 of the first embodiment. The oxygen saturation image processor 100 has only one correlation in its correlation memory 84. A correlation updater 101 substituting for the correlation selector 85 is another example of the changing section for changing the calculation method of the oxygen saturation level. The other components of the oxygen saturation image processor 100 are the same as those of the oxygen saturation image processor 82 of the first embodiment.

Figure 15:
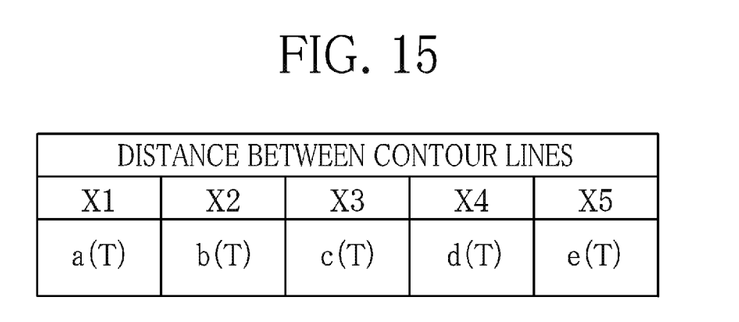
FIG. 15 is a table listing the distances X1 to X5 of contour lines that are defined by a cumulative lighting time T of the xenon lamp.

The correlation updater 101 updates the correlation stored in the correlation memory 84 based on the cumulative lighting time T of the xenon lamp measured by the timer 36 and a correlation update program installed in the memory 74. By running the correlation update program, the distances X1 to X5 of the contour lines 88a to 88f are changed in accordance with the cumulative lighting time T. More specifically, as shown in FIG. 15, the distances X1 to X5 are defined by functions "a(T)" to "e(T)" of the cumulative lighting time T. The oxygen saturation level calculator 86 calculates the oxygen saturation level of each pixel with the use of the intensity ratios B1/G2 and R2/G2 and the updated correlation.

In the first and second embodiments, the cumulative lighting time of the xenon lamp is used as spectrum change information, which is information about the variation in the emission spectrum of the broad band light BB, but other information may be used instead. For example, a balance among the measurement blue image data B1, the green image data G2, and the red image data R2 used in production of the oxygen saturation image gradually varies with the change in the emission spectrum of the xenon lamp with a lapse of time. Accordingly, the intensity ratios B1/G2 and R2/G2 come to deviate from their initial values. It can be said that there is a correlation between a deviation Δ of the intensity ratios and the variation in the emission spectrum of the broad band light BB. Therefore, the deviation Δ of the intensity ratios is usable as the spectrum change information, which relates to the variation in the emission spectrum of the broad band light BB.

In an endoscope system that uses the deviation Δ as the spectrum change information, a color measuring step is performed at first in the oxygen saturation level measurement mode. In the color measuring step, the deviation Δ is measured, and the correlation is updated based on the deviation Δ. To be more specific, the intensity ratios B1/G2 and R2/G2 of each pixel are obtained. Then, the intensity ratios B1/G2 and R2/G2 of all pixels are averaged to obtain an average value of each intensity ratio with respect to one frame of the oxygen saturation image.

Figure 16:
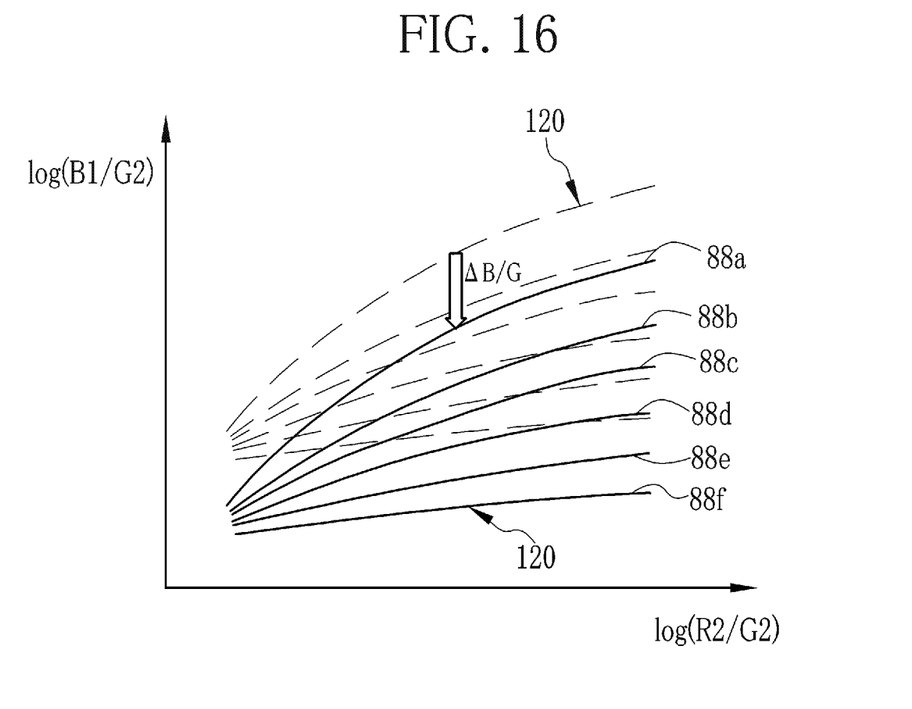
FIG. 16 is a graph in which all the contour lines are shifted based on a deviation of the intensity ratios from their initial values.

As to the intensity ratio B1/G2, a deviation Δ(B/G) between the initial value and the average value is calculated. As to the intensity ratio R2/G2, a deviation Δ(R/G) between the initial value and the average value is calculated. Based on the deviations Δ(B/G) and Δ(R/G), a contour line group including all the contour lines 88a to 88f is shifted in such a direction as to eliminate the deviations Δ(B/G) and Δ(R/G). For example, if the deviation Δ(B/G) is a positive value, a contour line group 120 including all the contour lines 88a to 88f is shifted to a negative direction with respect to a lateral axis, i.e. to a lower direction. After the color measuring step, the oxygen saturation level is calculated based on the correlation after the shift of the contour line group 120, as in the case of the oxygen saturation level measurement mode of the first embodiment.

Instead of shifting the contour line group 120 based on the deviations Δ(B/G) and Δ(R/G), each of the distances X1 to X5 of the contour lines may be adjusted based on the deviations Δ(B/G) and Δ(R/G). Also, in the case of using the light source including the phosphor instead of the xenon lamp, the calculation method of the oxygen saturation level may be changed using the deviations Δ in the intensity ratios from their initial values as the spectrum change information. The change in the calculation method of the oxygen saturation level includes, for example, "selecting one of a plurality of correlations suited for the spectrum change information" as with the first embodiment, and "updating the correlation by adjusting the distances of the contour lines" as with the second embodiment.

The above embodiments adopt a frame sequential method in which the monochrome image sensor captures images sequentially under irradiation with the measurement, B, G, and R light. Instead of the frame sequential method, a simultaneous method may be used in which a color image sensor images the internal body portion irradiated with the broad band light BB. In the case of the simultaneous method, for example, the broad band light BB including blue excitation light having a center wavelength of 473 nm and green to red fluorescence emitted from a phosphor excited by the blue excitation light is applied to the internal body portion. This broad band light BB much has a component having a wavelength band of 450 to 500 nm and a component having a wavelength band of 540 to 700 nm. The color image sensor, which is composed of B pixels having a blue filter, G pixels having a green filter, and R pixels having a red filter, captures an image under irradiation with the broad band light BB.

By imaging the body portion with the color image sensor, three colors i.e. blue, green, and red image data is obtained. The blue image data includes a component having a wavelength of 450 to 500 nm. The green image data includes a component having a wavelength of 540 to 580 nm. The red image data includes a component having a wavelength of 590 to 700 nm. The oxygen saturation level is calculated based on the intensity ratio B/G between the blue and green image data and the intensity ratio R/G between the red and green image data. Note that, the intensity ratio B/G corresponds to the intensity ratio B1/G2 of the above first and second embodiments. The intensity ratio R/G corresponds to the intensity ratio R2/G2 of the first and second embodiments.

In the above embodiments, the oxygen saturation level is calculated from the intensity ratios B1/G2 and R2/G2 obtained from the image data of three wavelength bands (measurement blue image data B1, green image data G2, and red image data R2). Instead of this, the oxygen saturation level may be calculated only from the intensity ratio B1/R2 obtained from the image data of two wavelength bands (measurement blue image data B1 and green image data G2).

In the above embodiments, the oxygen saturation image is produced using the oxygen saturation level, which is the ratio of oxyhemoglobin to blood volume (the sum of oxyhemoglobin and deoxyhemoglobin). Instead of or in addition to this, the oxygen saturation image may be produced using an oxyhemoglobin index calculated by "blood volume×oxygen saturation level (%)" or a deoxyhemoglobin index calculated by "blood volume×(100-oxygen saturation level) (%)".

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. An endoscope system comprising:
a light source that applies first illumination light to an object, said first illumination light having a first wavelength band in which oxyhemoglobin and deoxyhemoglobin have different absorption coefficients, wherein said light source further applies second illumination light having a second wavelength band and third illumination light having a third wavelength band to said object;
an imaging device that images said object and obtaining first image information under irradiation with said first illumination light, wherein said imaging device further obtains second image information under irradiation with said second illumination light and third image information under irradiation with said third illumination light;
a processing circuitry including a memory for storing a correlation among an oxygen saturation level of blood, a first intensity ratio being an intensity ratio of each pixel between a first image information pair chosen out of said first to third image information, and a second intensity ratio being an intensity ratio of each pixel between a second image information pair different from said first image information pair, wherein said correlation is represented in the form of a two dimensional table in which contour lines representing the oxygen saturation level of blood are defined in two-dimensional space and a position and a shape of the contour lines are determined by physical simulation of light scattering, the processing circuitry configured for:
obtaining spectrum change information relating to change in a spectrum of said first illumination light;
changing said correlation based on said spectrum change information; and
calculating said oxygen saturation level by using said first, second, and third image information and said changed correlation, wherein a cumulative lighting time of said lighting section is used as said spectrum change information, and wherein said memory is configured to store first and second correlations, wherein the first correlation is used when the cumulative lighting time is less than a predetermined value and the difference in the absorption coefficient between oxyhemoglobin and deoxyhemoglobin is within a predetermined range and the second correlation is used when the cumulative lighting time equals or exceeds the predetermined value and the difference in the absorption coefficient between oxyhemoglobin and deoxyhemoglobin is out of the predetermined range.

2. The endoscope system according to claim 1, wherein said first wavelength band is 400 to 500 nm;
said second wavelength band is 590 to 700 nm; and
said third wavelength band is 540 to 580 nm.

3. The endoscope system according to claim 1, wherein said changing section chooses one of said correlations based on said spectrum information obtained by said spectrum information obtaining section.

4. The endoscope system according to claim 1, wherein said changing section updates said correlation based on said spectrum information obtained by said spectrum information obtaining section.

5. The endoscope system according to claim 1, wherein a deviation between a measurement value and a predetermined initial value of an average value of at least one of said first and second intensity ratios is used as said spectrum change information.

6. The endoscope system according to claim 1, wherein said lighting section has a xenon lamp.

7. A processing circuitry of an endoscope system, said endoscope system including an endoscope device for imaging an object and obtaining a first image information under irradiation with a first illumination light having a first wavelength band in which oxyhemoglobin and deoxyhemoglobin have different absorption coefficients, wherein said endoscope device further images said object and obtains a second image information under irradiation with a second illumination light having a second wavelength band and a third image information under irradiation with a third illumination light having a third wavelength band, said processing circuitry comprising:

a receiver that receives said first image information under irradiation with said first illumination light, said second image information under irradiation with said second illumination light and said third image information under irradiation with said third illumination light;

a memory that stores a correlation among an oxygen saturation level of blood, a first intensity ratio being an intensity ratio of each pixel between a first image information pair chosen out of said first to third image information, and a second intensity ratio being an intensity ratio of each pixel between a second image information pair different from said first image information pair, wherein said correlation is represented in the form of a two dimensional table in which contour lines representing the oxygen saturation level of blood are defined in two-dimensional space and a position and a shape of the contour lines are determined by physical simulation of light scattering, the processor configured for:

obtaining spectrum change information relating to change in a spectrum of said first illumination light; and changing said correlation based on said spectrum change information, calculating said oxygen saturation level by using said first, second, and third image information and said changed correlation, wherein a cumulative lighting time of said lighting section is used as said spectrum change information, and wherein said memory is configured to store first and second correlations, wherein the first correlation is used when the cumulative lighting time is less than a predetermined value and the difference in the absorption coefficient between oxyhemoglobin and deoxyhemoglobin is within a predetermined range and the second correlation is used when the cumulative lighting time equals or exceeds the predetermined value and the difference in the absorption coefficient between oxyhemoglobin and deoxyhemoglobin is out of the predetermined range.

8. An image processing method for processing an image obtained by an endoscope device, said endoscope device obtaining a first image information by imaging an object under irradiation with a first illumination light having a first wavelength band in which oxyhemoglobin and deoxyhemoglobin have different absorption coefficients, wherein said endoscope device further images said object and obtains a second image information under irradiation with a second illumination light having a second wavelength band and a third image information under irradiation with a third illumination light having a third wavelength band, said image processing method comprising the steps of:

receiving said first image information under irradiation with said first illumination light, said second image information under irradiation with said second illumination light, and said third image information under irradiation with said third illumination light;

storing a correlation among an oxygen saturation level of blood, a first intensity ratio being an intensity ratio of each pixel between a first image information pair chosen out of said first to third image information, and a second intensity ratio being an intensity ratio of each pixel between a second image information pair different from said first image information pair, wherein said correlation is represented in the form of a two dimensional table in which contour lines representing the oxygen saturation level of blood are defined in two-dimensional space and a position and a shape of the contour lines are determined by physical simulation of light scattering;

obtaining spectrum change information relating to change in a spectrum of said first illumination light;

changing said correlation based on said obtained spectrum change information;

calculating said oxygen saturation level by using said first, second, and third image information and said changed correlation;

using a cumulative lighting time of said lighting section as said spectrum change information; and wherein said storing step is configured to store first and second correlations, wherein the first correlation is used when the cumulative lighting time is less than a predetermined value and the difference in the absorption coefficient between oxyhemoglobin and deoxyhemoglobin is within a predetermined range and the second correlation is used when the cumulative lighting time equals or exceeds the predetermined value and the difference in the absorption coefficient between oxyhemoglobin and deoxyhemoglobin is out of the predetermined range.

* * * * *